| United States Patent [19] | [11] Patent Number: 4,980,176 |
| Berke et al. | [45] Date of Patent: Dec. 25, 1990 |

[54] PRESERVATIVE COMPOSITIONS AND USES THEREOF

[75] Inventors: Philip A. Berke, Madison; William E. Rosen, Summit, both of N.J.

[73] Assignee: Sutton Laboratories, Inc., Chatham, N.J.

[21] Appl. No.: 34,609

[22] Filed: Apr. 6, 1987

Related U.S. Application Data

[63] Continuation of Ser. No. 836,130, Mar. 4, 1986, abandoned.

[51] Int. Cl.$^5$ ...................... A01N 59/06; A01N 43/80
[52] U.S. Cl. .................................. 424/682; 514/372; 514/561
[58] Field of Search ................ 514/372, 561; 424/682

[56] References Cited

U.S. PATENT DOCUMENTS 4,105,431  8/1978  Lewis et al. .......................... 514/372
4,337,269  6/1982  Berke et al. .......................... 514/561
4,661,503  4/1987  Martin et al. ........................ 514/372

Primary Examiner—Leonard Schenkman
Attorney, Agent, or Firm—Bacon & Thomas

[57] ABSTRACT

Compositions of matter containing a compound which is a member selected from the group consisting of hydroxymethylaminoacetic acids, its salts and lower alkyl esters, and one or more 3-isothiazolones are disclosed. The compositions provide synergistic microbial growth inhibition and biocidal activity in a wide range of substances requiring antimicrobial protection.

5 Claims, No Drawings

PRESERVATIVE COMPOSITIONS AND USES THEREOF

This application is a continuation of application Ser. No. 836,130, filed Mar. 4, 1986, now abandoned.

BACKGROUND OF THE INVENTION

1. Technical Field of the Invention

This invention is directed to compositions of matter containing a hydroxymethylaminoacetic acid derivative and one or more 3-isothiazolone compounds and their use to kill microorganisms and to inhibit microbial growth.

2. Description of the Prior Art

Hydroxymethylaminoacetic acid, its salts and lower alkyl esters, are known to be effective antimicrobial agents. Sodium hydroxymethylaminoacetate (CTFA Adopted Name: Sodium Hydroxymethylglycinate) is the active ingredient in the antimicrobial product marketed under the trademark Suttocide ® A.

U.S. Pat. Nos. 4,105,431 and 4,252,694, disclose a group of compounds generally referred to as 3-isothiazolones, having biocidal properties. Kathon ® is the trademark for a family of biocides containing these compounds as active ingredients. More specifically, the Kathon ® biocides contain an aqueous mixture of 5-chloro-2-methyl-4-isothiazolin-3-one and 2-methyl-4-isothiazolin-3-one in various weight ratios between about 2:1 and 4:1, respectively, with magnesium salts added as stabilizers. Kathon ® formulations have been proposed by the manufacturer for use as a biocide in various industrial applications, such as in cooling-tower water, metalworking fluids, latex emulsions and for slime control in paper mills. They have also been proposed as a biocide for swimming pool water and as an antimicrobial preservative for toiletries, cosmetics and household cleaning products. However, a significant drawback to the 3-isothiazolone compounds is their high toxicity, particularly their high corrosiveness and skin sensitizing properties.

SUMMARY OF THE INVENTION

We have discovered that the combination of a hydroxymethylaminoacetic acid derivative with one or more biocidal 3-isothiazolones exhibits synergistic biocidal and antimicrobial activity against a wide range of microorganisms.

The synergistic combination has a wide range of applications, including all areas where the Kathon ® family of biocides and preservatives are currently employed. The synergistic combination, advantageously, provides greater effectiveness, reduced costs and lower toxicological exposure of workers and consumers to the severe skin sensitizing properties of the 3-isothiazolones.

Accordingly, it is a primary object of the invention to provide a composition of matter comprising (i) hydroxymethylaminoacetic acid, its salts or lower alkyl esters and (ii) one or more compounds of the formula (I):

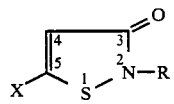
(I)

wherein R is a lower alkyl group, preferably methyl, and X is hydrogen or a halogen, preferably chlorine. By incorporating an effective amount of this composition into a substance requiring microbial inhibition, the substance can be protected against a variety of microorganisms including bacteria, yeast and mold.

DETAILED DESCRIPTION OF THE PREFERRED EMBODIMENTS

The hydroxymethylaminoacetic acid component of the composition of the invention is prepared as described in U.S. Pat. No. 4,337,269, the disclosure of which is hereby incorporated by reference. As described therein, in preparing this component, a mixture of glycine and a basic reagent, such as an alkali metal hydroxide, is prepared and mixed with formaldehyde in a molar ratio of glycine to formaldehyde of about 1:1. To obtain a salt other than the alkali metal salt, a compound which will cause replacement of the alkali metal cation is added to the reaction mixture. In this manner, numerous salts can be prepared including aluminum hydroxymethylaminoacetate, calcium hydroxymethylaminoacetate, magnesium hydroxymethylaminoacetate, copper hydroxymethylaminoacetate and zinc hydroxymethylaminoacetate. When alkyl glycinates are reacted in place of glycine, alkyl hydroxymethylaminoacetates are produced. Of these esters, lower alkyl esters, e.g., methyl hydroxymethylaminoacetate are most preferred.

After the reaction is complete, an equilibrium mixture of reaction products is obtained as a relatively clear, aqueous solution. The final form of the product may be a solution or a crystalline powder which is readily dissolved in aqueous media.

The 3-isothiazolones used in the composition of the invention are prepared as described in the previously cited U.S. Pat. Nos. 4,252,694 and 4,105,431, the disclosures of which are hereby incorporated by reference. As described therein, these compounds can be prepared by the cyclization of a substituted disulfide-amide having the formula (II):

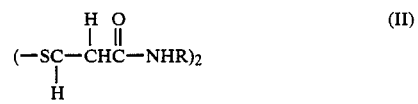
(II)

where R is as previously defined. The cyclization is accomplished by reacting the disulfide-amide with a halogenating agent. Any halogenating agent may be employed in this reaction. Typical halogenating agents include chlorine, bromine, sulfuryl chloride, sulfuryl bromide, N-chlorosuccinimide, N-bromosuccinimide, iodine monochloride, etc. Bromine and chlorine are preferred halogenating agents. Cyclization of the disulfide-amide will take place when 3 mole equivalents of halogeating agent are employed in the reaction. The cyclization reaction is typically carried out at a temperature in the range 0° to 100° C. in an inert, non-aqueous solvent, such as benzene, toluene, xylene, ethyl acetate, or ethylene dichloride. When R is methyl in the disulfide-amide reactant of formula (II), 2-methyl-4-isothiazolin-3-one is obtained. By providing an excess of halogenating agent, the isothiazolone can be halogenated at the 5-position, giving 5-chloro-2-methyl-4-isothiazolin-3-one, when the halogenating agent is chlorine.

The 3-isothiazolones present in the Kathon ® formulations are aqueous mixtures of 5-chloro-2-methyl-4-isothiazolin-3-one and 2-methyl-4-isothiazolin-3-one. These compounds are present in ratios, by weight, between 2:1 and 4:1 as the active ingredients in the formulations. The formulations additionally contain magnesium salts, such as magnesium nitrate and magnesium chloride, as stabilizers, and water.

Synergism between two antimicrobials is exhibited when the observed activity of the combination is greater than the expected additive activity of the two separate antimicrobials. We have discovered that the combination of our Suttocide® A formulation which is an aqueous solution of sodium hydroxymethylaminoacetate with a Kathon® formulation exhibits synergism in both microbial inhibition and microbiocidal activity. The synergistic activity appears in Suttocide® to Kathon® ratios, by weight, from less than 2:1 to approximately 60:1. Because the Kathon® formulations are highly diluted with water and magnesium salts, the actual ratio of active ingredients in the combination of Suttocide® A and Kathon® will be much higher, on the order of approximately 100:1 to 4000:1.

The examples which follow report our experiments carried out with a Kathon® formulation identified as Kathon® CG (cosmetic grade), a popular formulation used as a preservative in cosmetics and toiletries, and Suttocide® A. The composition of Kathon CG is:

| Active ingredients | |
|---|---|
| 5-chloro-2-methyl-4-isothiazolin-3-one | 1.15% |
| 2-methyl-4-isothalizon-3-one | 0.35% |
| Inert Ingredients | |
| Magnesium salts | 23.0% |
| Water | 75.5% |
| | 100.0% |

Suttocide® A is sodium hydroxymethylaminoacetate (100% active ingredient).

The results reported are considered to be applicable to all Kathon® formulations, since the active ingredients are the same, as well as formulations based upon other isothiazolones of formula (I) in combination with Suttocide A or other hydroxymethylaminoacetic acid derivatives previously described.

EXAMPLE 1

A minimum inhibitory concentration was determined for each component and their combination versus the following challenge inocula:

*Pseudomonas aeruginosa*: ATCC #9027
*Candida albicans*: ATCC #10231
*Aspergillus niger*: ATCC #16404

Each sample series was diluted 1:1 using 5 mls. of Trypticase Soy Broth and 5 mls. of product. The same procedure was used to prepare the yeast and mold challenge samples except the dilution broth used was Sabouraud Dextrose Broth. All diluted samples were then inoculated using 0.1 cc of each challenge inocula. All tubes were incubated at 37° C. for 24 to 48 hours and then examined for turbidity. The "MIC" for each product is the last clear tube before the first tube showing turbidity.

Table 1 lists minimum inhibitory concentrations (MIC) of Suttocide® A (100% basis) and Kathon® CG (1.5% solution) for a gramnegative bacterium, *Pseudomonas aeruginosa* (ATCC No. 9027), a yeast *Candida albicans* (ATCC No. 10231), and a mold, *Aspergillus niger* ATCC No. 16404). MICs are the minimum concentrations at which each antimicrobial or combination prevents growth of microorganisms. A combination of half the amount of Suttocide® A plus half the amount of Kathon® CG would be expected to be the minimum required level needed to inhibit growth if the activities are additive. If combination quantities containing less than half of each are inhibiting, it demonstrates greater than expected activity, and therefore synergism between the two antimicrobials.

TABLE 1

| Minimum Inhibitory Concentrations (all concentrations in ppm) | | | |
|---|---|---|---|
| | P. aeruginosa (ATCC 9027) | C. albicans (ATCC 10231) | A. niger (ATCC 16404) |
| Suttocide® A(100% active ingredient) | 313 | 1250 | 313 |
| Kathon® CG(1.5% active ingredient) | >333 | 42 | 21 |
| Expected MIC (half concentrations) Suttocide® A/ Kathon® CG | 157/>167 | 625/21 | 157/11 |
| Observed MIC Suttocide® A/ Kathon® CG | 157/83 | 157/21 | 157/0.67 or 79/1.33 |

The data recorded in Table 1 demonstrates that for combinations of the two antimicrobials, the observed MIC's for the combinations of Suttocide® A and Kathon® CG was less than the expected MIC's based upon the results for each antimicrobial individually tested reduced to half concentrations. These results for the combination of Suttocide® A and Kathon® clearly demonstrate synergism in the combination.

EXAMPLE 2

A minimum concentration for a killing (biocidal) effect was determined for each component and their combination on *E. coli* (ATCC #8739), a coliform bacterium.

The bacteria were cultivated, plated and maintained in Trypticase Soy Broth (TSB) and/or Trypticase Soy Agar (TSA). All bacterial dilutions were done using TSB.

For each compound a set-up entailed a total of 10–12 test tubes with each tube containing 2.5 ml of the appropriate concentration of the compound and 2.5 ml of the appropriate test organism. The concentration of the organism was adjusted to about $10^6$/ml and this was confirmed by standard plate counts.

All test tubes containing compound plus *E. coli* were then incubated at 37° C. for 24, 48, and 72 hrs. After each period of incubation 0.01 ml (10 μl) from each tube was dispensed into appropriate sterile agar plates. The plates were then incubated at 37° C. for 24–48 hours and the resulting colonies counted.

The counts were compared with the original counts. This comparison permitted the determination of 97–100% kill for each compound at each concentration tested. Less than 97% kill was reported as growth. The lowest concentration of compound or combination of compounds for which 97–100% kill occurred was the minimum biocidal concentration (MBC).

The results of this test are recorded in Table 2.

TABLE II

| Minimum Biocidal Concentrations (all concentrations in ppm) | |
|---|---|
| | E. coli (ATCC 8739) |
| Suttocide® A (100% active ingredient) | 625 |

TABLE II-continued

| Minimum Biocidal Concentrations (all concentrations in ppm) | E. coli (ATCC 8739) |
|---|---|
| Kathon ® CG (1.5% active ingredients) | 160 |
| Expected MBC (half concentrations) Suttocide ® A/Kathon ® CG | 313/80 |
| Observed MBC Suttocide ® A/Kathon ® CG | 313/53 |

The results show that the MBC for the combination of Suttocide ® A and Kathon ® was less than half of each antimicrobial individually tested reduced to half concentrations.

The synergistic microbial inhibiting and biocidal activity of the combination of hydroxymethylaminoacetic acid, its salts and lower alkyl esters and the 3-isothiazolones, has significant practical applications since it allows lesser amounts of the 3-isothiazolone components to be used to achieve an equivalent microbial inhibiting or biocidal effect. This is important since the 3-isothiazolones are notoriously corrosive and highly irritating to skin. Hence, the composition of the present invention can be used in all applications where the 3-isothiazolones, particularly the Kathon ® family of products have been proposed, with less toxicities.

Such applications include, but are not limited to, use as an antimicrobial preservative in cosmetics, toiletries and household cleaning properties, use as a biocide for synthetic latexes, emulsion paints and other coatings, adhesives, polishes, carpet backing compositions, surfactants, metalworking fluids, industrial and domestic water treatment including cooling tower systems and swimming pools, adhesive mats, drilling mud formulations, painting pastes, spin finish emulsions, polymer dispersions, fuels and in other substances susceptible to contamination by microorganisms. A further important application is as a slimicide for slime control in the manufacture of paper from wood pulp.

The amount of the composition of the invention incorporated into a product will, of course, depend upon the particular product being treated as well as the purpose of the treatment, i.e., preservative or biocide. Generally, amounts to no greater than 1.0%, by weight based upon the weight of the product, of active ingredients will be effective for most uses. However, it is understood that due to the diversity in applications in which the composition may be used, this weight percentage is not an absolute maximum.

The composition of the invention may be incorporated into a product requiring antimicrobial protection by pre-mixing the individual components, e.g., Suttocide ® A and Kathon ®, in a common carrier and then incorporating the pre-mixed composition into the product or by incorporating the individual components into the product separately. The invention, therefore, contemplates both pre-mixed compositions containing the antimicrobial components as well as compositions which are prepared only as part of the formulation of a product requiring antimicrobial protection. In either case, the preferred compounds and weight ratios of these compounds to one another are the same. In particular, the combination of sodium hydromethylaminoacetate with 5-chloro-2-methyl-4-isothiazolin-3-one and 2-methyl-4-isothiazolin-3-one in which the weight ratio of 5-chloro-2-methyl-4-isothiazolin-3-one to 2-methyl-4-isothiazolin-3-one is between about 2:1 and 4:1 is most preferred. This composition is obtained by formulating the product to be preserved with effective amounts of Suttocide ® A (sodium hydroxymethylaminoacetate) and any one of the numerous Kathon ® formulations.

While the invention has now been described in terms of certain preferred embodiments, and exemplified with respect thereto, one skilled in the art will readily appreciate that various modifications, changes, omissions and substitutions may be made without departing from the spirit thereof. It is intended, therefore, that the present invention be limited solely by the scope of the following claims.

What is claimed is:

1. A composition of matter comprising sodium hydroxymethylaminoacetate, 5-chloro-2-methyl-4-isothiazolin-3-one and 2-methyl-4-isothiazolin-3-one, wherein the ratio, by weight, of 5-chloro-2-methyl-4-isothiazolin-3-one to 2-methyl-4-isothiazolin-3-one is between about 2:1 and 4:1 and the ratio, by weight, of sodium hydroxymethylaminoacetate to the sum of the weights of 5-chloro-2-methyl-4-isothiazolin-3-one and 2-methyl-4-isothiazolin-3-one is between about 100:1 and about 4000:1.

2. The composition of claim 1, further comprising magnesium salts and water.

3. A method for inhibiting microbial growth in a substance requiring microbial inhibition comprising incorporating into the substance an effective microbial growth inhibiting amount of the composition of claim 1.

4. A preserved product comprising an effective microbial growth inhibiting amount of the composition of claim 1.

5. A method for killing microorganisms comprising contacting said microorganisms with an effective biocidal amount of the composition of claim 1.

* * * * *